United States Patent [19]

Hallon et al.

[11] Patent Number: 4,751,928

[45] Date of Patent: Jun. 21, 1988

[54] MULTIELECTRODE SYSTEM FOR SURFACE REGISTERING OF ELECTRIC HEART POTENTIALS

[75] Inventors: Jozef Hallon; Andrej Zachar, both of Bratislava, Czechoslovakia

[73] Assignee: Slovenska akdemie vied Bratislava, Bratislava, Czechoslovakia

[21] Appl. No.: 59,905

[22] Filed: Jun. 9, 1987

[30] Foreign Application Priority Data

Jun. 11, 1986 [CS]  Czechoslovakia ............... 4303-86

[51] Int. Cl.$^4$ .............................................. A61B 5/04
[52] U.S. Cl. ..................................... 128/644; 128/696
[58] Field of Search ............... 128/639, 644, 695, 696, 128/731, 733, 741, 783, 798, 799, 802

[56] References Cited

U.S. PATENT DOCUMENTS

| | | | |
|---|---|---|---|
| 2,318,207 | 5/1943 | Ellis | 128/644 |
| 2,549,836 | 4/1951 | McIntyre | 128/644 |
| 3,490,439 | 1/1970 | Rolston | 128/644 |
| 4,202,344 | 5/1980 | Mills et al. | 128/644 |
| 4,275,743 | 6/1981 | Hjort | 128/644 |
| 4,457,309 | 7/1984 | Elmeskog | 128/644 |
| 4,517,983 | 5/1985 | Toyosu et al. | 128/639 |

FOREIGN PATENT DOCUMENTS

| | | | |
|---|---|---|---|
| 0068032 | 4/1982 | European Pat. Off. | |
| 1355600 | 2/1964 | France | 128/644 |
| 274612 | 7/1951 | Switzerland | 128/644 |

OTHER PUBLICATIONS

Lexa et al., '37 Electrode for a Multi-Electrode Bipotential Pickup System", Czechoslovakian Authorship Certificate No. 216,690, Published 3/15/84 (with English Language Translation).

Primary Examiner—William E. Kamm
Attorney, Agent, or Firm—Klein and Vibber

[57] ABSTRACT

A multielectrode system for surface registering of electric heart potentials comprising electrodes which are in an elastic holder of electrodes arrranged slidably and are maintained in their position by a clamping device, enabling a quick adjustment of the position of each electrode with respect to the elastic electrode holder in order to achieve a good contact with the surface of the body of a patent.

3 Claims, 2 Drawing Sheets

MULTIELECTRODE SYSTEM FOR SURFACE REGISTERING OF ELECTRIC HEART POTENTIALS

FIELD OF THE INVENTION

The invention relates to electrodes and a multielectrode system for surface registering of electric heart potentials.

BACKGROUND OF THE INVENTION

For picking up heart potentials by the noninvasive method, it is known to use either independent electrodes where each electrode is separately fixed on the body surface, or a number of electrodes, mounted on suitable elastic holders. A common drawback of all of the known electrodes is that a film of a conductive gel must be applied on their contact surface. A further drawback of known multielectrodes is that a good contact between the body of the patient and the electrode is not possible is cases of pathological deformation of the breast of the patient. The proper preparation and application of multielectrodes requires up to ¾ of an hour. The whole process is time consuming and the cleaning of electrodes from the conductive gel is wearisome. Moreover, insufficiently cleaned electrodes become electrically not conductive.

SUMMARY OF THE INVENTION

It is an object of this invention to reduce substantially said drawbacks of similar multielectrode systems for surface registration of electric heart potentials. The electrode according to this invention comprises an elastic contact body inserted into the lower end of an electrically conductive tube which in turn is inserted into an insulating body supported by a resilient holder of the multielectrode, with clamping means fixed to said insulating body adapted to maintain the electrode in a desired position.

One advantage of this invention is that the resilient contact body is adapted to compensate for all possible small unevenesses on the breast of the patient and to secure a reliable contact. In the case of larger pathological recesses of the breast, a simple and quick establishment of a contact between the electrode and the body of the patient can be achieved. All electrodes are, prior to picking up of potentials, soaked simultaneously in an electrically conductive solution and the cleaning of all electrodes is similarly performed simultaneously by rinsing. The soaking, application of electrodes and the picking up takes about seven minutes.

BRIEF DESCRIPTION OF THE DRAWING

With these and other objects in view, which will become apparent in the following detailed description, the present invention, which is shown by example only, will be clearly understood in connection with the accompanying drawing, in which.

DESCRIPTION OF THE PREFERED EMBODIMENT

Figure 1:
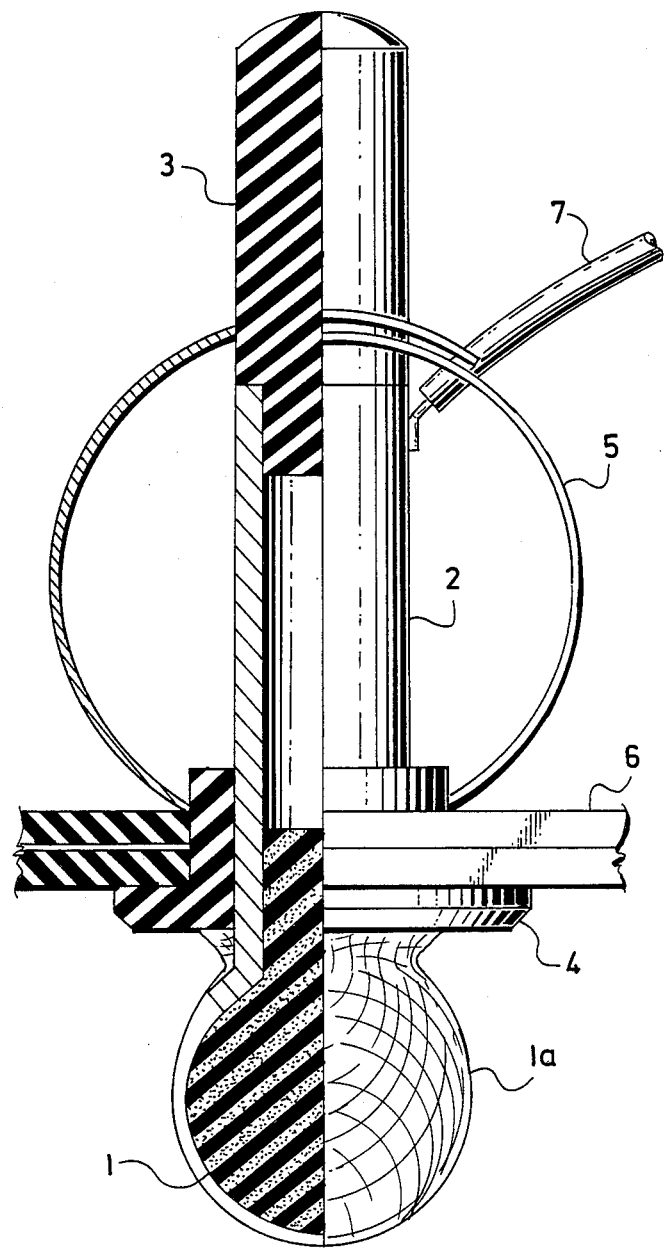
FIG. 1 is a cross sectional elevation of a single electrode in a multielectrode holder.

Referring to FIG. 1, the electrode of the multielectrode system comprises a resilient contact body 1 which is inserted into an electrically conductive tube 2, which can be advantgeously of silver or silver plated, whereby the contact body 1 can be fastened at the lower part of the tube 2 for instance by a gauze 1a fixed to the spaced apart end of the tube 2 by a thread (not shown). A pin 3 of insulating material is inserted into and fixed to the tube 2 at the top. An electric conductor 7 is fixed to the tube 2.

Insulating inserts 4 for supporting electrodes are fixed permanentaly to the elastic holder 6 having openings corresponding to the external diameter of tubes 2 of the electrodes which are inserted into said insulating inserts in sliding fashion. Clamping means 5 are provided on the insulating inserts 4 adapted to secure the correct position of electrodes with respect to the elastic holder 6. In the example shown, the clamping means are represented by spring collets, the lower part of which is fixed to the insulating insert 4, the upper part of which rests against the insulating pin 3 inserted from the top of the conductive tube 2. Any other clamping means can be, of course, used for this purpose.

Figure 3:
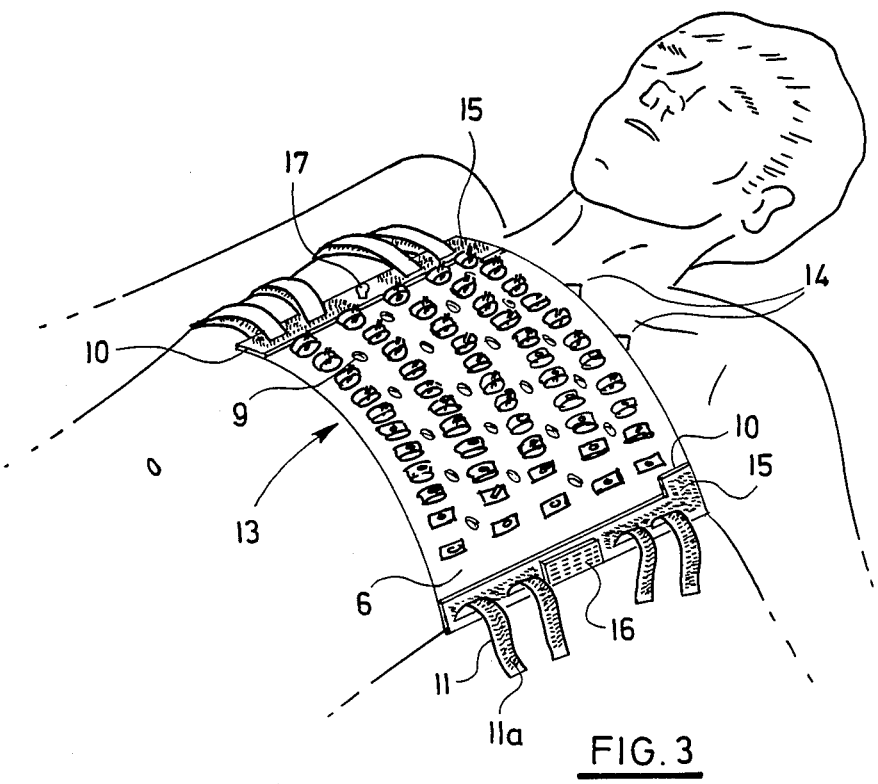
FIG. 3 shows the multielectrode fastened on the body of a patient.

Referring to FIGS. 1 and 3, the thus arranged electrode is supported in an elastic holder 6 of the multielectrode 13 (FIG. 3) composed of, e.g., two rubber plates placed one on the other which are mutually fastened by gluing on a number of places, leaving however spaces for passage of conductors 7 leading from individual electrodes which conductors are thus protected from damage in the course of operation.

Referring to FIG. 3, venting openings 9 are provided in the elastic holder 6 serving the patient and simultaneously the cardiologist for making markings on the skin of the patient in case a control investigation should be performed.

Up to 50 electrodes can be thus supported by the elastic holder 6. In normal operation, however, it is seldom that all 50 electrodes are used simultaneously, generally 35 electrodes are sufficient for the purpose of the cardiologist. The holder 6 is reinforced by elastic strips 10 on both opposite sides. The elastic strips 10 are provided with fixing means 15, for example the so-called "dry zip" or "velcro". Straps 11 are attached to the strips 10 and are also provided with similar fixing means 11a. In FIG. 3, straps 11 are shown in a position where the connection of straps is loosened. Naturally, any other means serving this fixing/connection purpose can be used.

The holder 6 is also provided with a socket 16 concentrating all conductor 7 leading from individual electrodes (FIG. 1), fixed on one side of the multielectrode 13 and a handle 17 on its other side used in order to manipulate the position of multielectrode 13. Markers 14 are advantageously provided on the top part of the elastic holder 6.

Figure 2:
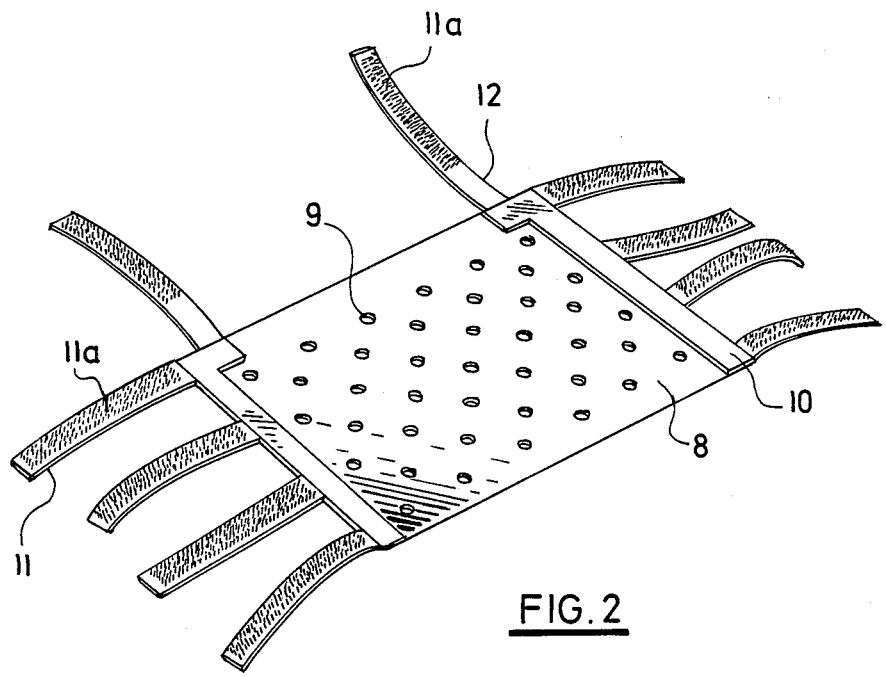
FIG. 2 is a view of a fastening belt

In order to maintain the multielectrode 13 on site, a fastening belt 8 is provided, shown in FIG. 2. The fastening belt 8, which resembles the elastic holder 6, is designed to be arranged on the back of the patient. Like the elastic, holder 6, the fastening belt is also provided with venting openings 9 and with reinforcing elastic strips 10 on both opposite sides, to which strips 10, connecting straps 11, are fixed and provided with parts 11a of "dry zip" or "velcro". In addition, shoulder straps 12 with similar parts 11a are fixed on the upper side of this fastening belt 8, which straps 12 are used only if a patient has to be investigated in a sitting position.

In the case of application of the multielectrode 13 to a patient who has to be investigated in a horizontal position, the fastening belt 8 is first laid on a bed so that the topmost connecting straps 11 comes just below the arms of the patient. After the patient has laid down on the bed, the cardiologist takes the multielectrode 13 with his left hand by the handle 17 and with his right hand by the multicable socket 16 and places the multielectrode 13 on the chest of the patient so that one of the marks 14 comes to the center of the chest bone. He connects thereafter the connecting straps 11 of the fastening belt 8 with corresponding 15 of the multielectrode 13 which is thus secured in its correct position. After a multiple plug has been connected to the socket 16, the multielectrode 13 is prepared for operation. In case a zero line from some electrode is registered on the cardiograph, indicating that no correct contact has been established between the skin of the patient and the respective electrode, the insulating pin 3 of said electrode has to be pressed down until a good contact is obtained and amplitudes are shown on the record.

In case a patient is investigated in the sitting position, the shoulder strap 12 is fastened to parts 15 maintaining the multielectrode 13 in its correct positon. After the investigation is finished, the multiple plug is disconnected from the socket 16, the connecting straps 11, possibly also the shoulder strap 12, are loosened and the electrodes of the multielectrode 13 are rinsed by a stream of water.

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. A multielectrode system for surface registering of electric heart potentials comprising
   a plurality of electrically conductive tubes, each of said tubes having an upper part and a lower part;
   a corresponding plurality of resilient contact bodies, each resilient contact body being inserted into the lower part of a corresponding one of said conductive tubes;
   means for fixing said resilient contact bodies to said tubes;
   a corresponding plurality of insulating pins, each of said pins being fixed to the upper part of a corresponding one of said tubes;
   an elastic multielectrode holder, said holder being provided with a plurality of openings, with insulating inserts penetrating said openings and fixed to said holder;
   said insulating inserts provided with openings corresponding to the external diameter of said conductive tubes;
   each one of said conductive tubes being embraced by one of said insulating inserts whereby said tubes are slidable through the openings of said inserts;
   a plurality of clamping means, each of said clamping means being adapted to retain one of said tubes in a desired position in one of said insulating inserts.

2. A multielectrode system for surface registering of electric heart potentials as claimed in claim 1, wherein each of said electrically conductive tubes have a surface and said surface is silver.

3. A multielectrode system for surface registering of electric heart potentials as claimed in claim 1, wherein each of said clamping means comprises a spring collet, the lower part of which is fixed to a corresponding on of said insulating inserts of the elastic multielectrode holder, the upper part of said collet resting against the insulating pin inserted into the conductive tube of the electrode.

* * * * *